United States Patent [19]

Bailey

[11] Patent Number: 4,590,183

[45] Date of Patent: May 20, 1986

[54] GASTRIC CYTOPROTECTION WITH SODIUM THIOSULFATE IN ORAL ADMINISTRATION OF ASPIRIN

[75] Inventor: Denis M. Bailey, East Greenbush, N.Y.

[73] Assignee: Sterling Drug Inc., New York, N.Y.

[21] Appl. No.: 725,447

[22] Filed: Apr. 22, 1985

[51] Int. Cl.⁴ .............................................. A61K 31/61
[52] U.S. Cl. ................................................... 514/163
[58] Field of Search ................................ 514/163, 164

[56] References Cited

U.S. PATENT DOCUMENTS 3,988,466  10/1977  Takagi et al.
4,016,268  4/1977   Goldenberg et al.
4,491,574  1/1985   Seifter et al.

FOREIGN PATENT DOCUMENTS 2318649  2/1977  France .

OTHER PUBLICATIONS

Sodium Thiosulfate, The Merck Index, Eighth Edition, 1968, pp. 967–968.
Sodium Thiosulfate, The Merck Index, Tenth Edition, 1983, item 8542 (p. 1243).
Fasth et al., Biochemical Pharmacology, 22, 1337–1351 (1973), entitled "Protective Effect of Thiosulfate and Metabolic Thiosulfate Precursors Against Toxicity of Nitrogen Mustard ($HN_2$)".

*Primary Examiner*—Stanley J. Friedman
*Attorney, Agent, or Firm*—Robert K. Bair; B. Woodrow Wyatt; Paul E. Dupont

[57] ABSTRACT

The method of providing cytoprotection of the gastric mucosa in a mammal receiving aspirin perorally which comprises orally administering either prior to or in combination with aspirin a cytoprotectively effective amount of sodium thiosulfate alone or in combination with a pharmaceutically acceptable carrier. Also shown is a composition for providing cytoprotection of the gastric mucosa in a mammal receiving aspirin perorally which comprises aspirin in combination with a cytoprotectively effective amount of sodium thiosulfate.

20 Claims, No Drawings

GASTRIC CYTOPROTECTION WITH SODIUM THIOSULFATE IN ORAL ADMINISTRATION OF ASPIRIN

BACKGROUND OF THE INVENTION (a). Field of the Invention

This invention relates to gastric cytoprotection in oral administration of aspirin.

(b). Information Disclosure Statement

Takagi et al in U.S. Pat. No. 3,988,466, issued Oct. 26, 1977, show that gastric lesions induced by aspirin or indomethacin are prevented by administration of amino acids, in particular, L-glutamine, L-lysine and L-arginine.

Goldenberg et al in U.S. Pat. No. 4,016,268, issued Apr. 5, 1977, show that bismuth subsalicylate co-administered with aspirin or other antiinflammatory drugs combats gastric ulceration associated with such drugs.

Seifter et al in U.S. Pat. No. 4,491,574, issued Jan. 1, 1985 show the use of the vitamin A or precursor thereof in a method of reducing toxicity and inhibiting ulcerogenesis and bleeding in the stomach of a mammal due to the ingestion of aspirin. This reference also cites a number of other publications pertaining to various means for inhibiting the gastric ulcerogenic effects of aspirin or other antiinflammatory agents, e.g., indomethacin.

Sodium thiosulfate, as shown in THE MERCK INDEX, Eighth Edition, 1968, pages 967–8, in addition to having a wide variety of non-medicinal uses, has been used as an antidote for cyanide poisoning, in some thrombotic conditions, topically for tinea versicolor, and, formerly for arsenical dermatitis. Also, it is said to have low human toxicity. As shown in THE MERCK INDEX, Tenth Edition, 1983, item 8542 (p. 1243), sodium thiosulfate is said to be useful in various veterinary indications in cats, e.g., antidote in cyanide poisoning, as a "general detoxifier", in bloat, and externally in ringworm, mange.

Fasth et al, Biochemical Pharmacology 22, 1337–1351 (1973), published a paper entitled "Protective Effect of Thiosulfate and metabolic Thiosulfate Precursors Against Toxicity of Nitrogen Mustard ($HN_2$)".

Van Moorleghem French Patent Publication No. 2,318,649, published Feb. 18, 1977, pertains to medicaments containing bisublimed iodine, sodium or potassium iodide, an alkaline salt, a plasma substitute, an analgesic, anti-inflammatory and antipyretic, and an anesthetic agent, said medicaments useful for the treatment of rheumatism and cancer. A typical composition was prepared from the following solutions: 0.10 g iodine and 0.20 g of potassium iodide dissolved in 2 ml of water (soln. A); 0.266 g of magnesium thiosulfate in 2 ml of water (soln. B); 5 ml. of 25% polyvinyl pyrrolidone (soln. C); 0.5 g of aspirin and 0.05 g of sodium glycerophosphate in 5 ml of water (soln. D); and, 0.05 g of diethylamino 2,6-dimethylacetanilide hydrochloride, 5 mg of methyl p-hydroxybenzoate and an excipient to 5 ml (soln. E). Solutions A and B were mixed together until decolorized and solutions C, D and E added.

SUMMARY OF THE INVENTION

In a method aspect the invention resides in the method of providing cytoprotection of the gastric mucosa in a mammal receiving aspirin perorally which comprises orally administering either prior to or in combination with aspirin a cytoprotectively effective amount of sodium thiosulfate alone or in combination with a pharmaceutically acceptable carrier.

In another method aspect the invention resides in the method of preventing or inhibiting gastric lesions in a mammal receiving aspirin perorally which comprises orally administering either prior to or in combination with aspirin a cytoprotectively effective amount of sodium thiosulfate alone or in combination with a pharmaceutically acceptable carrier.

In a composition aspect the invention resides in a composition for providing cytoprotection of the gastric mucosa in a mammal receiving aspirin perorally which comprises aspirin in combination with a cytoprotectively effective amount of sodium thiosulfate.

DETAILED DESCRIPTION INCLUSIVE OF PREFERRED EMBODIMENTS

Various studies or experiments were carried out to demonstrate the effectiveness of sodium thiosulfate as a gastric cytoprotective agent in said method aspects of the invention. Fasted Sprague-Dawley female rats were given intragastrically (ig) at least four different doses ranging from 1–30 mg/100 g. body weight of sodium thiosulfate either 30 minutes before or parallel with intragastric administration of 10 mg/100 g body weight of acidified aspirin. Rats were killed one hour after aspirin administration and the number of hemorrhagic gastric erosions (or lesions) was determined and the area of erosion was measured by computerized planimetry. Sodium thiosulfate coadministered with aspirin was found to offer significant ($p<0.01$) gastric cytoprotection, the minimum statistically significant effective dose for sodium thiosulfate as its pentahydrate being about 5 mg/100 g. and for anhydrous sodium thiosulfate being about 3 mg/100 g. The effectiveness of sodium thiosulfate as cytoprotectant against aspirin-induced gastric lesions was also demonstrated in arthritic rats using the standard pharmacological antiinflammatory adjuvant-induced arthritis assay wherein it also was established that sodium thiosulfate did not reduce the antiinflammatory efficacy of aspirin. Also, it was shown that sodium thiosulfate and the coadministered combination of sodium thiosulfate with aspirin had a low order of toxicity.

Said composition aspect of the invention can be prepared by combining the aspirin and sodium thiosulfate alone or in combination with a pharmaceutically acceptable excipient or carrier in conventional dosage forms such as capsules, tablets, caplets, and the like. A preferred embodiment of said composition contains in a gelatin capsule a mixture of aspirin and sodium thiosulfate, said mixture alone or in combination with a pharmaceutically acceptable excipient, such as starch, silica or other conventional formulating excipient or additive. Because aspirin and sodium thiosulfate in admixture do not have extended shelf life at room temperature (25° C.) and above as shown hereinbelow, said composition is freshly prepared shortly before use. Alternatively, it is contemplated that the aspirin and sodium thiosulfate can be formulated so that the aspirin and sodium thiosulfate are isolated from each other, for example, by encapsulating the particles of either or both with a suitable polymeric coating such as ethylcellulose or hydroxypropyl methylcellulose prior to formulation, or by interposing an inert barrier between the ingredients, for example by pelletizing one of the two ingredients, placing the pellet in a gelatin capsule, covering the pellet with a pharmaceutically acceptable inert excipient such as starch or silica and then adding the second ingredient, or by placing each ingredient in separate layers of a multilayered tablet having an inert barrier between the layers.

Ordinarily the composition will contain from about 0.5 to 1.5 part by weight of sodium thiosulfate per part of aspirin, preferably about equal parts by weight the two ingredients. More sodium thiosulfate, up to about three parts by weight per part of aspirin, can be used. Smaller amounts of sodium thiosulfate can be used, i.e., as low as about 0.15 part of sodium thiosulfate per part by weight of aspirin. The actual weights of said ingredients per unit dosage form depends on the dosage of aspirin to be administered, such normal adult doses as 325 mg, 500 mg, 650 mg and 1 g. Smaller doses of course are used for children and in some instances larger doses may be used as an adult dosage.

In preparing in conventional manner tablets containing said ingredients, there may be incorporated prior to or during tabletting the conventional tabletting aids or excipients, such as binders, disintegrants, lubricants, plasticizers, diluents, colors, surfactants or wetting agents, and the like. Illustrative of these excipients are: *binders*—microcrystalline cellulose, lactose, sucrose; *disintegrants*—corn or potato starch, sodium starch glycolate; *lubricants*—magnesium stearate, talc, stearic acid, silicon dioxide; *diluents*—lactose, sucrose; *plasticizers*—glycerine, glyceryl triacetate, propylene glycol, polyethylene glycol 4000 or 6000; *surfactants*—sodium lauryl sulfate.

Sodium thiosulfate can be used either as its pentahydrate or, preferably, in its anhydrous form.

In carrying out the method aspect the aspirin and sodium thiosulfate can be coadministered using said composition aspect or the sodium thiosulfate and aspirin can be administered in separate unit dosage forms either simultaneously or sequentially, i.e., the sodium thiosulfate followed by the aspirin. Dosage regimen, i.e., frequency of administration, is well known in aspirin therapy.

There follows examples and experiments which demonstrate the effectiveness of the method and composition aspects of the invention. Thus, the following test results are exemplary of the present aspirin therapy improvement as applied to mammals and as demonstrated with rats. It is known to those skilled in the art of pharmaceutical chemistry that the experiments performed on animals as illustrated herein are indicative of corresponding effects in humans. The following examples will further illustrate the invention without, however, limiting it thereto.

EXAMPLE 1

Protection Against Aspirin-Induced Hemorrhagic Gastric Erosions and Mucosal Vascular Injury By Sodium Thiosulfate All of the experiments in this example were performed in female Sprague-Dawley rats having an initial body weight of 150–200 g. The animals housed under 12 hour light and dark cycles initially had an unlimited access to Purina ® laboratory chow and tap water. Before the administration of aspirin, the rats were fasted overnight. Every group (control and experimental) consisted of 3–4 rats and each experiment was repeated at least twice and the results were pooled. The extent of gastric mucosal injury was evaluated by a Zeiss stereomicroscope coupled with a computerized planimeter which allowed both surface measurement and counting of lesions, according to the published method of Sandor Szabo et al entitled "A Quantitative Method for Assessing the Extent of Experimental Gastric Erosions and Ulcers", J. Pharmacological Methods 13, 59–66, 1985. Light microscopy of formalin-fixed sections was also performed.

Aspirin was suspended in 1% methylcellulose dissolved in 200 mM HCl and was administered at 10 mg/100 g body weight by gavage with rubber tube (Rusch No. 8) and rats were killed one hour later. The study design is presented as follows in Table A.

TABLE A

| Study Design | |
|---|---|
| Compound: | Sodium thiosulfate as its pentahydrate |
| Doses: | 0, 1, 5, 10, 30 mg/100 g body weight |
| Time: | Aspirin: 0 min. |
| | Compound: −30, −0.5 min. |
| | Autopsy: +60 min. |

In the initial experiment, doses of sodium thiosulfate as its pentahydrate were given per os (p.o.) either 30 minutes or 30 seconds before aspirin. The 30 second pretreatment is virtually a parallel administration of the compounds. The intragastric gavage of aspirin immediately followed the administration of sodium thiosulfate pentahydrate. In these experiments sodium thiosulfate pentahydrate when given 30 minutes before aspirin exerted a dose-dependent protection against aspirin-induced gastric erosions.

In the parallel administration protocol, the minimum statistically signficant effective dose (MED) of sodium thiosulfate pentahydrate was 5 mg/100 g on the basis of both area of lesions and number of lesions, as seen from Tables B and C, wherein the data are expressed respectively as percentage of glandular stomach area and as total number of erosions.

TABLE B

Effect of Sodium Thiosulfate Pentahydrate On Aspirin-induced Gastric Mucosal Erosions In Rats (Data expressed as percentage of glandular stomach area)

| Dose[a] | 0 | 1.0 | 5.0 | 10.0 | 30.0 |
|---|---|---|---|---|---|
| | 1.42 | 0.89 | 0.18* | 0.27* | 0* |
| S.E. | ±0.32 | ±0.42 | ±0.05 | ±0.16 | ±0.00 |
| N | 19 | 9 | 9 | 9 | 9 |

[a]Single oral dose (mg/100 g body weight); aspirin given concomitantly at 10 mg/100 g in acidified 1% methylcellulose and rats sacrificed 1 hour after drug administration.
*$p<0.01$

TABLE C

Effect of Sodium Thiosulfate Pentahydrate On Aspirin-induced Gastric Mucosal Erosions In Rats (Data expressed as total number of erosions)

| Dose[a] | 0 | 1.0 | 5.0 | 10.0 | 30.0 |
|---|---|---|---|---|---|
| | 11.90 | 6.67 | 1.56* | 1.78* | 0* |
| S.E. | ±2.16 | ±3.32 | ±0.44 | ±1.29 | ±0.00 |
| N | 19 | 9 | 9 | 9 | 9 |

[a]Single oral dose (mg/100 g body weight); aspirin given concomitantly at 10 mg/100 g in acidified 1% methylcellulose and rats sacrificed 1 hour after drug administration.
*$p<0.01$ The minimum statistically significant effective dose (MED) of sodium thiosulfate pentahydrate was about 5 mg/100 g or about 50 mg/kg, i.e., about 201 μmol/kg. The absolute MED of sodium thiosulfate in anhydrous form is about 32 mg/kg.

The above experiments indicate that coadministration of nontoxic doses of sodium thiosulfate (as its pentahydrate) decrease or abolish aspirin-induced gastric mucosal lesions.

EXAMPLE 2

Gastric Cytoprotection Against Aspirin Lesions In Adjuvant Arthritic Rats Using Sodium Thiosulfate Male Sprague-Dawley rats (initial weight of 280–353 g) received single oral daily doses of anhydrous sodium thiosulfate at either 150 or 300 mg/kg for 16 days coadministered with 150 mg/kg of aspirin in an adjuvant-induced arthritis assay [C. J. Pearson, "Experimental Joint Disease", J. Chron. Dis. 16, 863–874 (1963); E. M. Glenn and J. Grey, "Adjuvant Induced Polyarthritis in Rats: Biologic and Histologic Background", Amer. J. Vet. Res. 26, 1180–1193 (1965)]. At the completion of the assay the stomachs were excised and examined for the presence or absence of lesions. Coadministration of sodium thiosulfate at 150 mg/kg with 150 mg/kg of aspirin resulted in fewer lesions (mean of 3.4), when compared with aspirin alone (mean of 15.2); and, the mean size of the lesions was also reduced, being 3.19 mm$^2$ for sodium thiosulfate with aspirin compared with 16.02 mm$^2$ for aspirin alone. Coadministration of 300 mg/kg of sodium thiosulfate with 150 mg/kg of aspirin resulted in a mean number of lesions of 7.2 compared with a mean number of lesions of 25.7 for aspirin alone; and, the mean size of the lesions was also reduced with coadministration of sodium thiosulfate with aspirin, being 3.73 mm$^2$ compared with 11.61 mm$^2$ for aspirin alone. Sodium thiosulfate was effective in reducing the number and size of lesions induced with aspirin when coadministered for 16 days at 150 and 300 mg/kg with aspirin at 150 mg/kg, although it appeared that a plateau of effectiveness had been reached at the lower dose level of the sodium thiosulfate. No enhancement of cytoprotective activity was determined at the higher dose level. Results of these studies are given below in Tables D and E.

TABLE D

Cytoprotection Against Aspirin Lesions In Adjuvant Arthritis Study

| Group (mg/kg)$^a$ | No. of Rats with Lesions | Mean ± S.E. Area of Lesion (mm$^2$) | No. of Lesions |
|---|---|---|---|
| Controls | 0/10 | 0 | 0 |
| Aspirin 150 | 10/10 | 16.02 ± 3.82 | 15.2 ± 2.9 |
| Na thiosulfate 150 | 1/5 | 0.12 ± 0.12 | 0.4 ± 0.4 |
| Asprin 150 + Na thiosulfate 150 | 4/5 | 3.19 ± 1.62 | 3.4* ± 1.2 |

*Significantly different from control; p≦0.05
$^a$Single daily oral administration for 16 days

TABLE E

Cytoprotection Against Aspirin Lesions In Adjuvant Arthritis Study

| Group (mg/kg)$^a$ | No. of Rats with Lesions | Mean ± S.E. Area of Lesion (mm$^2$) | No. of Lesions |
|---|---|---|---|
| Controls | 1/10 | 0.04 ± 0.04 | 0.1 ± 0.1 |
| Aspirin 150 | 9/9 | 11.61 ± 4.42 | 25.7 ± 4.9 |
| Na thiosulfate 300 | 0/5 | 0 | 0 |
| Aspirin 150 + Na thiosulfate 300 | 5/5 | 3.73 ± 2.20 | 7.2* ± 2.5 |

*Significantly different from control; p≦0.01
$^a$Single daily oral administration for 16 days

EXAMPLE 3

Effect of Coadministration of Sodium Thiosulfate With Aspirin On Acute Inflammation In Rats Male Sprague-Dawley rats (initial weight of about 200 g.) received a single oral dose of sodium thiosulfate (anhydrous) at either 30, 100 or 300 mg/kg coadministered with 100 mg/kg of aspirin in the carrageenin model of acute inflammation (paw edema) [C. A. Winler et al, "Carrageenin-Induced Edema in Hind Paw of the Rat as an Assay for Anti-Inflammatory Drugs", Proc. Soc. Exptl. Biol. Med. 111, 544–547 (1962)] and it was found that this coadministration of sodium thiosulfate with aspirin did not appear to influence the anti-inflammatory efficacy of aspirin.

Results of these studies are given in Table F which also includes data for the standard phenylbutazone.

TABLE F

Effect of Coadministration of Sodium Thiosulfate With Aspirin On Acute Inflammation In Rats

| Compound | Dose, mg/kg | Mean Paw Edema, ml + S.E. | % Inhibition |
|---|---|---|---|
| Control |  | 1.16 ± 0.1 |  |
| Aspirin | 100 | 0.65 ± 0.1 | 44* |
| Na thiosulfate + Aspirin | 30 100 | 0.51 ± 0.04 | 56* |
| Na thiosulfate + Aspirin | 100 100 | 0.50 ± 0.02 | 57* |
| Na thiosulfate + Aspirin | 300 100 | 0.47 ± 0.04 | 59* |
| Phenylbutazone | 100 | 0.41 ± 0.03 | 65* |

*Significantly different from control; p≦0.01.
Number of rats per group were 9.

EXAMPLE 4

Effect of Coadministration of Sodium Thiosulfate With Aspirin On Chronic Inflammation In Rats Male Sprague-Dawley rats (initial weight of 225 to 250 g.) received single oral daily doses of sodium thiosulfate (anhydrous) at either 150 or 300 mg/kg for 16 days either alone or coadministered with 150 mg/kg of aspirin in said adjuvant-induced arthritis assay. It was found that sodium thiosulfate did not demonstrate an effect on the development of arthritis and, also, that its coadministration with aspirin did not influence the anti-inflammatory efficacy of aspirin. Results of these studies are given below in Tables G and H.

TABLE G

Effect of Coadministration of Sodium Thiosulfate With Aspirin On Adjuvant Arthritis In Rats

| Compound | Dose mg/kg | Injected Hind Paw Volume ml + S.E. | % Inhibition |
|---|---|---|---|
| Adjuvant Control | — | 5.57 ± 0.4 | — |
| Normal Control | — | 1.89 ± 0.03 | — |
| Aspirin | 150 | 3.31 ± 0.2 | 61* |
| Na thiosulfate | 150 | 5.21 ± 0.5 | 10 |
| Na thiosulfate + Aspirin | 150 150 | 3.49 ± 0.1 | 57* |

*Significantly different from control; p≦0.01
Number rats per group were 9 or 10

TABLE H

Affect of Coadministration of Sodium Thiosulfate With Aspirin On Adjuvant Arthritis In Rats

| Compound | Dose mg/kg | Injected Hind Paw Volume ml + S.E. | % Inhibition |
|---|---|---|---|
| Adjuvant Control | — | 5.36 ± 0.4 | — |
| Normal Control | — | 1.87 ± 0.1 | — |
| Aspirin | 150 | 3.85 ± 0.3 | 43* |

TABLE H-continued

Affect of Coadministration of Sodium Thiosulfate With Aspirin On Adjuvant Arthritis In Rats

| Compound | Dose mg/kg | Injected Hind Paw Volume ml + S.E. | % Inhibition |
|---|---|---|---|
| Na thiosulfate | 300 | 5.30 ± 0.4 | 2 |
| Na thiosulfate + Aspirin | 300 150 | 3.91 ± 0.3 | 42* |

*Significantly different from control; $p \leq 0.01$
Number rats per group 9 or 10

EXAMPLE 5

Acute Toxicity of Sodium Thiosulfate In Rats

Sodium thiosulfate (anhydrous) was given as a single oral dose to male Sprague-Dawley rats weighing approximately 116-140 g to determine its approximate acute oral $LD_{50}$. The rats were fasted for four hours before medication, observed for seven days following medication and all surviving rats sacrificed and necropsied at the completion of the study. Sodium thiosulfate thus was found to have an $ALD_{50}$ of 7,000 mg/kg (7 days). This indicated a low order of acute toxicity although gastric irritancy was observed at this very high dose level.

EXAMPLE 6

Capsules containing various mixtures of aspirin or aspirin-starch granulation with sodium thiosulfate are shown in Examples 6-9.

25 Capsules containing a 50:50 mixture of anhydrous sodium thiosulfate (325 mg) and aspirin (325 mg) were prepared. The capsules were then assayed for aspirin and free salicylic acid and the contents were examined for evaluation of compatibility of two said ingredients.

| Formula | mg/capsule | x 30 capsules |
|---|---|---|
| 1. Na thiosulfate | 325 | 9.75 g |
| 2. Aspirin | 325 | 9.75 g |
| Capsule fill wt. | 650 | |
| Approx. empty cap. wt. | 100 | |
| Total filled cap. wt. | 750 | |

Procedure:
1. Weigh ingredients 1 and 2.
2. Triturate each separately in a mortar to a fine particle size.
3. Combine the two, blending well.
4. Encapsulate into size O capsules, with a target fill weight of 650 mg, each total filled capsule weighing approximately 750 mg. The actual weight range was from 736 to 753 mg, the average weight being 745 mg.
5. 25 capsules were filled, stored in an amber glass vial with metal screw cap closure having a pressure-sensitive ethyl vinyl acetate liner, kept at 25° C. for seven days, and then analyzed for aspirin and free salicylic acid by standard ultraviolet spectrometry [K. Kitamura et al, Chem. Pharm. Bull. 32 (4), 1484-1490 (1984)]

Analysis:
After 7 days at 25° C., the quantity of aspirin found per capsule by said standard ultraviolet spectrometric analytic procedure was 312.5, 325.0 and 321.2 mg. No salicylic acid was detected.

After 65 days at 25° C., the quantity of aspirin found per capsule by the HPLC assay procedure detailed hereinbelow (Ex. 10) was 98.2% and 96.4% mg. The quantity of salicylic acid found per capsule was 1.8% and 1.78%.

EXAMPLE 7

The procedure of this example was like that of Example 6 but using 406 mg of an 80/20 aspirin-starch granulation (containing 325 mg of aspirin) in place of 325 mg of aspirin (ASA).

| Formula | mg/capsule | x 30 capsules |
|---|---|---|
| 1. Na thiosulfate | 325 | 9.75 g |
| 2. 80/20 ASA-starch granulation | 406 | 12.18 g |
| Capsule fill wt. | 731 | |
| Approx. empty cap. wt. | 100 | |
| Total filled cap. wt. | 831 | |

Procedure:
1. Weigh both ingredients.
2. Triturate the sodium thiosulfate crystals in a mortar to a fine particle size.
3. Triturate the ASA-starch granulation in a mortar to reduce the size of the large granules.
4. Combine the two ingredients, blending well.
5. Encapsulate into size O capsules, with a target fill weight of 731 mg and a total filled capsule weight of 831 mg. The actual weight range was from 816 to 841 mg, the average weight being 830 mg.
6. 25 Capsules were filled, stored in an amber glass vial with metal screw cap closure having a pressure-sensitive ethyl vinyl acetate liner, kept at 25° C. for seven days, and then analyzed as in Example 6.

Analysis:
After 7 days at 25° C., the quantity of aspirin found per capsule by said ultraviolet spectrometric procedure was 312.5, 312.5 and 337.5 mg. No salicylic acid was detected.

After 65 days at 25° C., the quantity of aspirin found per capsule by said HPLC assay procedure was 96.9%. The quantity of salicylic acid found per capsule was 2.2%.

EXAMPLE 8

This example was carried out following the procedure of Example 6 but using 50 mg instead of 325 mg of sodium thiosulfate and using size 1 rather than size O capsules.

| Formula | mg/capsule | x 30 capsules |
|---|---|---|
| 1. Sodium thiosulfate | 50 | 1.50 g |
| 2. Aspirin | 325 | 9.75 g |
| Capsule fill wt. | 375 | |
| Empty cap. wt. | 80 | |
| Total filled cap. wt. | 455 | |

There was thus obtained 25 filled capsules ranging in weight from 447 to 464 mg and averaging 455 mg. These were stored as in Example 6 at 25° C. for four days and analyzed.

Analysis:
After 4 days at 25° C., the quantity of aspirin found per capsule by said ultraviolet spectrometric procedure was 312.5, 321.2 and 328.2 mg., and no salicylic acid was detected.

After 62 days at 25° C., the quantity of aspirin found per capsule by said HPLC assay procedure was 97.6% and the quantity of salicylic acid found per capsule was 0.9%.

EXAMPLE 9

This example was carried out following the procedure of Example 7 but using 50 mg instead of 325 mg of sodium thiosulfate and using size 1 rather than size O capsules.

| Formula | mg/capsule | x 30 capsules |
|---|---|---|
| 1. Sodium thiosulfate | 50 | 1.50 g |
| 2. 80/20 ASA-starch granulation | 406 | 12.18 g |
| Capsule fill wt. | 456 | |
| Empty cap. wt. | 80 | |
| Total filled cap. wt. | 536 | |

There was thus obtained 25 filled capsules ranging in weight from 529 to 548 mg and averaging 538 mg. These capsules were stored as in Example 7 at 25° C. for four days and analyzed.

Analysis:

After 4 days at 25° C., the quantity of aspirin found per capsule by said ultraviolet spectrometric procedure was 325, 325 and 325 mg, and no salicylic acid was detected.

After 62 days at 25° C., the quantity of aspirin found per capsule by said HPLC assay procedure was 95.5% the quantity of salicylic acid found per capsule was 0.9%.

EXAMPLE 10

Objective:

To study the stability at 25° C., 40° C. (75% RH) and 70° C. of mixtures of aspirin (ASA) with sodium thiosulfate (STS), and 80/20 ASA-starch granulation (ASA-SG) with sodium thiosulfate (STS).

Combinations:
(a) ASA 325 mg plus STS 325 mg.
(b) ASA 325 mg plus STS 50 mg.
(c) ASA-SG 406 mg plus STS 325 mg.
(d) ASA-SG 406 mg plus STS 50 mg.

Stress Conditions:
(a) 25° C.
(b) 40° C./75% RH (relative humidity)
(c) 70° C.

Procedure of Preparation:

All samples were prepared by grinding the combination in a mortar with pestle. Samples were well mixed, stored in amber glass vials with metal screw cap closures each having a pressure-sensitive ethyl vinyl acetate liner, and placed in the stress chambers. Samples were withdrawn for HPLC analysis after one week.

HPLC Assay:

This method separates aspirin and salicylic acid by high pressure liquid chromatography (HPLC). Sample mixtures are extracted with methanol, suitably diluted and chromatographed using the MCH-10 (Varian) 4.6×25 mm column. The mobile phase consists of 40% A and 60% B (A- 0.02% phosphoric acid, B-methanol). The mobile phase was run at 2 ml/min and the UV detector was set at 285 NM. The retention time of aspirin is 3.1 min. and that of salicylic acid is 5.3 min.

| Combination (mgs.) | Stress Temp.°C. | % ASA | % SA | Physical Appearance |
|---|---|---|---|---|
| Results after one week: | | | | |
| ASA325 + STS325 | 70 | 29.0 | 36.2 | sticky wet mass |
| Control (ASA) | 70 | 100 | none | no change |
| ASA325 + STS50 | 70 | 86.8 | 5.2 | white powder |
| ASA325 + STS325 | 40[a] | 61.6 | 12.0 | white powder, caked |
| ASA325 + STS50 | 40[a] | 87.8 | 2.8 | white powder, caked |
| Control (ASA) | 40[a] | 98.8 | none | no change |
| ASA-SG406 + STS325 | 70 | — | — | caked |
| Control (80/20ASA-SG) | 70 | 99.9 | none | no change |
| ASA-SG406-STS50 | 70 | — | — | caked |
| ASA-SG406-STS325 | 40[a] | — | — | caked, sulfide odor |
| Control (80/20ASA-SG) | 40[a] | 101.6 | none | no change |
| ASA-SG406-STS50 | 40[a] | — | none | caked, sulfide odor |
| Control (80/20ASA-SG) | 40[a] | 101.6 | none | no change |
| ASA325 + STS325 | 25 | — | — | white powder, sulfide odor |
| ASA325 + STS50 | 25 | — | — | no change |
| ASA-SG406-STS325 | 25 | — | — | no change |
| ASA-SG406-STS50 | 25 | — | — | no change |
| Results after 2 months and 28 days: | | | | |
| ASA325 + STS325 | 25 | 79.8, 78.7 | 10.7, 11.1 | no change, sulfide odor |
| ASA325 + STS50 | 25 | 88.2, 89.5 | 8.3, 8.3 | no change, sulfide odor |
| Control (ASA) | 25 | 100.5, 100.5 | none | no change |
| ASA-SG406 + STS325 | 25 | 75.1, 74.5 | 15.7, 16.1 | no change, sulfide odor |
| ASA-SG406 + STS50 | 25 | 85.2, 84.4 | 12.6, 12.6 | no change, sulfide odor |
| Control (80/20ASA-SG) | 25 | 100.1, 100.1 | none | no change |

[a]75% relative humidity

I claim:

1. The method of providing cytoprotection of the gastric mucosa in a mammal receiving aspirin perorally which comprises orally administering either prior to or in combination with aspirin a cytoprotectively effective amount of sodium thiosulfate, using at least about 0.15 part of sodium thiosulfate per part by weight of aspirin.

2. The method according to claim 1 wherein the aspirin and sodium thiosulfate are administered in combination with a pharmaceutically acceptable carrier.

3. The method according to claim 1 wherein aspirin and sodium thiosulfate are administered in combination dosage form.

4. The method according to claim 1 wherein about 0.5 to 1.5 parts by weight of sodium thiosulfate and 1 part by weight of aspirin are administered in combination dosage form.

5. The method according to claim 1 wherein about equal parts by weight of sodium thiosulfate and aspirin are administered in combination dosage form.

6. The method according to claim 1 wherein aspirin and sodium thiosulfate are administered in separate dosage form.

7. The method of preventing or inhibiting gastric lesions in a mammal receiving aspirin perorally which comprises orally administering either prior to or in combination with aspirin a cytoprotectively effective amount of sodium thiosulfate, using at least about 0.15 part of sodium thiosulfate per part by weight of aspirin.

8. The method according to claim 7 wherein the aspirin and sodium thiosulfate are administered in combination with a pharmaceutically acceptable carrier.

9. The method according to claim 7 wherein aspirin and sodium thiosulfate are administered in combination dosage form.

10. The method according to claim 7 wherein about 0.5 to 1.5 parts by weight of sodium thiosulfate and 1 part by weight of aspirin are administered in combination dosage form.

11. The method according to claim 7 wherein about equal parts by weight of sodium thiosulfate and aspirin are administered in combination dosage form.

12. The method according to claim 7 wherein aspirin and sodium thiosulfate are administered in separate dosage form.

13. A composition for providing cytoprotection of the gastric mucosa in a mammal receiving aspirin perorally which comprises aspirin in combination with a cytoprotectively effective amount of sodium thiosulfate, using at least about 0.15 part of sodium thiosulfate per part by weight of aspirin.

14. A composition according to claim 13 comprising aspirin and sodium thiosulfate in combination with a pharmaceutically acceptable carrier.

15. A composition according to claim 13 wherein the aspirin and sodium thiosulfate are isolated from each other.

16. A composition according to claim 13 in unit dosage form comprising a mixture of aspirin and sodium thiosulfate in a gelatin capsule.

17. A composition according to claim 13 in unit dosage form comprising a mixture of aspirin and sodium thiosulfate in combination with a pharmaceutically acceptable excipient in a gelatin capsule.

18. A composition according to claim 13 comprising about 0.15 to 3 parts by weight of sodium thiosulfate per part of aspirin.

19. A composition according to claim 13 comprising about 0.5 to 1.5 parts by weight of sodium thiosulfate per part of aspirin.

20. A composition according to claim 13 comprising about equal parts by weight of sodium thiosulfate and aspirin.

* * * * *